United States Patent
Cook

(10) Patent No.: US 11,076,754 B2
(45) Date of Patent: Aug. 3, 2021

(54) ELECTRONIC ENDOSCOPE CLEANER SHEATH

(71) Applicant: Gyrus ACMI, Inc., Southborough, MA (US)

(72) Inventor: Christopher A. Cook, New York, NY (US)

(73) Assignee: Gyrus Acmi, Inc., Westborough, MA (US)

( * ) Notice: Subject to any disclaimer, the term of this patent is extended or adjusted under 35 U.S.C. 154(b) by 256 days.

(21) Appl. No.: 16/272,297

(22) Filed: Feb. 11, 2019

(65) Prior Publication Data

US 2019/0167088 A1  Jun. 6, 2019

Related U.S. Application Data

(63) Continuation of application No. 14/556,381, filed on Dec. 1, 2014, now Pat. No. 10,238,276.

(60) Provisional application No. 61/910,519, filed on Dec. 2, 2013.

(51) Int. Cl.
| | |
|---|---|
| *A61B 1/12* | (2006.01) |
| *A61B 1/00* | (2006.01) |
| *G02B 23/24* | (2006.01) |
| *G02B 27/00* | (2006.01) |
| *A61B 1/015* | (2006.01) |

(52) U.S. Cl.
CPC .......... *A61B 1/126* (2013.01); *A61B 1/00135* (2013.01); *A61B 1/015* (2013.01); *G02B 23/2476* (2013.01); *G02B 27/0006* (2013.01)

(58) Field of Classification Search
CPC .................................. A61B 1/126; B08B 3/12
See application file for complete search history.

(56) References Cited

U.S. PATENT DOCUMENTS

| | | | |
|---|---|---|---|
| 3,380,195 A | 4/1968 | Bodine, Jr. | |
| 5,458,633 A | 10/1995 | Bailey | |
| 5,830,127 A | 11/1998 | DeCastro | |
| 6,110,103 A | 8/2000 | Donofrio | |
| 8,419,625 B2 | 4/2013 | Ito | |
| 10,238,276 B2 | 3/2019 | Cook | |
| 2008/0188714 A1 | 8/2008 | McCaffrey | |
| 2009/0264701 A1 | 10/2009 | Ito | |
| 2009/0281478 A1 | 11/2009 | Duke | |
| 2010/0027705 A1 | 2/2010 | Neubauer et al. | |
| 2010/0327705 A1 | 12/2010 | Koyama | |
| 2011/0082336 A1 | 4/2011 | Ito | |
| 2011/0133578 A1 | 6/2011 | Choi | |
| 2011/0201888 A1 | 8/2011 | Verner | |

(Continued)

FOREIGN PATENT DOCUMENTS

JP  2013027625 A  2/2013

OTHER PUBLICATIONS

"U.S. Appl. No. 14/556,381, Final Office Action dated Jul. 24, 2018", 13 pgs.

(Continued)

*Primary Examiner* — Aaron B Fairchild
(74) *Attorney, Agent, or Firm* — Schwegman Lundberg & Woessner, P.A.

(57) ABSTRACT

An apparatus for cleaning a distal tip of an endoscope includes a driver configured to be mounted over a shaft of the endoscope, the driver adapted for generating transverse waves along a length of the shaft. The apparatus may be provided as a retrofit to existing equipment, or as a feature of new equipment. Methods of operation are disclosed.

10 Claims, 3 Drawing Sheets

(56) References Cited

U.S. PATENT DOCUMENTS

2013/0261437 A1 10/2013 Hennings et al.
2015/0150438 A1 6/2015 Cook

OTHER PUBLICATIONS

"U.S. Appl. No. 14/556,381, Non Final Office Action dated Nov. 29, 2017", 12 pgs.
"U.S. Appl. No. 14/556,381, Notice of Allowance dated Nov. 15, 2018", 10 pgs.
"U.S. Appl. No. 14/556,381, Response filed Mar. 27, 2018 to Non Final Office Action dated Nov. 29, 2017", 10 pgs.
"U.S. Appl. No. 14/556,381, Response filed Aug. 22, 2017 to Restriction Requirement dated Jul. 12, 2017", 2 pgs.
"U.S. Appl. No. 14/556,381, Response filed Sep. 24, 2018 to Final Office Action dated Jul. 24, 2018", 10 pgs.
"U.S. Appl. No. 14/556,381, Restriction Requirement dated Jul. 12, 2017", 6 pgs.
"International Application Serial No. PCT/US2014/067857, International Search Report dated Mar. 31, 2015", 3 pgs.

ELECTRONIC ENDOSCOPE CLEANER SHEATH

RELATED APPLICATIONS

This patent application is a continuation of U.S. application Ser. No. 14/556,381 filed Dec. 1, 2014, which claims the benefit under 35 U.S.C. § 119(e) of U.S. Provisional Patent App. No. 61/910,519, filed Dec. 2, 2013, entitled "ELECTRONIC ENDOSCOPE CLEANER SHEATH," which are hereby incorporated by reference in their entireties.

BACKGROUND OF THE INVENTION

1. Field of the Invention

The invention disclosed herein relates to surgical apparatus, and in particular to methods and apparatus for removing contamination from a distal end of an endoscope during use.

2. Description of the Related Art

A problem commonly encountered during use of an endoscope in a surgical procedure is contamination or fogging of a distal window during the procedure. The contamination can significantly limit visualization and render the instrument virtually useless. In many instances, this requires a practitioner to first remove the endoscope from the surgical site and then clean and dry the distal window before resuming surgery. This problem is particularly pronounced in procedures where tight spaces are concerned. For example, during arthroscopic procedures where the tip is close to the treatment site, contamination may easily adhere to the distal window rendering the instrument virtually useless.

One approach to solving this problem involves irrigation of the window. In this approach, a removable sheath is attached over the endoscope. The sheath directs a stream of saline or other liquid onto the distal window. The irrigating liquid is pumped to the sheath using a syringe or other pump. The irrigating liquid is provided to irrigate the surgical site and flush away any contamination from the distal window. One problem with this approach is that the residual liquid on the distal window can also significantly limit visualization. A drop of liquid clinging to the window can distort the image to the point where the procedure is interrupted. As with the contamination itself, the only option is to remove, dry, and reinsert the endoscope. Again, this leads to interruption of an ongoing surgical procedure.

One technique that attempts to overcome problems associated with deposition of excess liquid involves applying suction to eliminate the residual liquid. Generally, devices configured for applying suction include an additional channel for the suction into separate valves. One valve is provided for injection of irrigation liquid and another valve is provided for controlling the vacuum. Separate tubing is attached to the valves to connect them to external vacuum and irrigation sources. As one might imagine, such a system is bulky, complicated and can result in entanglement. Further, the additional apparatus make the endoscope heavier more cumbersome and less easy to manipulate. Another disadvantage is a reduction in the effective length of the endoscope.

Thus, there is a need for methods and apparatus to provide for effective cleaning of a distal tip of an endoscope while the endoscope is in active use. Preferably, the methods and apparatus are unobtrusive and simple to use during a procedure.

SUMMARY OF THE INVENTION

In one embodiment, an apparatus for cleaning a distal tip of an endoscope is disclosed. The apparatus includes a driver configured to be mounted over a shaft of the endoscope, the driver adapted for generating transverse waves along a length of the shaft.

In another embodiment, an apparatus for cleaning a distal tip of an endoscope is disclosed. The apparatus includes a driver configured to be mounted over a shaft of the endoscope, the driver adapted for generating transverse waves along a length of the shaft; a source configured for powering the driver; and a sheath configured for transmitting the waves.

In yet another embodiment, an endoscope is disclosed. The endoscope includes a shaft including a distal tip including a window for providing visualization; and a driver mounted over the shaft, the driver adapted for generating transverse waves along a length of the shaft.

BRIEF DESCRIPTION OF THE DRAWINGS

The features and advantages of the invention are apparent from the following description taken in conjunction with the accompanying drawings in which.

DETAILED DESCRIPTION OF THE INVENTION

A system for cleaning a distal tip of an endoscope during a surgical procedure is disclosed herein. The system includes methods and apparatus that may be used in conjunction with a conventional irrigating system used to wash away debris from a window of the endoscope. The system may be used to retrofit existing equipment or as design features of new equipment. Additionally, the methods and apparatus disclosed are simple and therefore cost effective to manufacture as well as easy to use.

Figure 1:
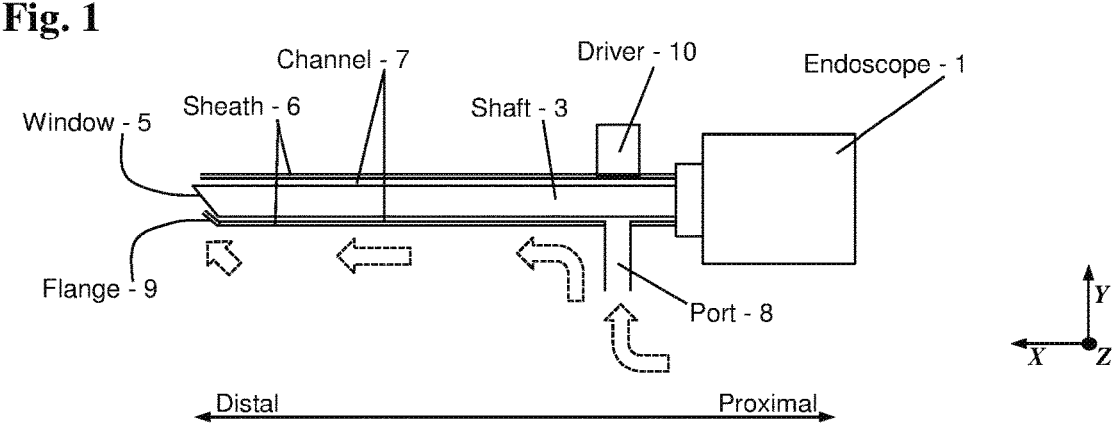
FIG. 1 is a schematic diagram depicting a side view of an exemplary endoscope.

Referring now to FIG. 1, there is shown an exemplary endoscope 1. Generally, the endoscope 1 includes apparatus as necessary for visualizing a surgical site. Merely for purposes of discussion, ancillary equipment as needed for operating the endoscope 1 is not shown. That is, it should be recognized that the depiction in FIG. 1 is simplified to focus on the system for cleaning the distal tip.

In this illustration, the endoscope 1 includes a shaft 3. At a distal tip of the shaft 3 is a window 5. During surgery, a practitioner will guide the shaft 3 and the distal tip to a surgical site. By operating the endoscope 1, the practitioner will be able to visually monitor the surgical site through the window 5.

The shaft 3 is surrounded by a sheath 6. Generally, the sheath 6 is removable and replaceable. Within the sheath 6 is a channel 7. The channel 7 receives an irrigating fluid through port 8. As shown by the dashed arrows, the irrigating fluid will travel from port 8 along a length of the shaft 3 through the channel 7 and generally out through optional flange 9.

Flange 9 is generally configured to direct the irrigating fluid over the window 5. Accordingly, when visualization becomes impaired, the practitioner may supply the irrigating fluid to the window 5. However, as one might imagine, with a very small window 5 residue of the irrigating fluid itself may enhance visual impairment. Accordingly, the exemplary endoscope 1 includes electromechanical driver 10. Prior to discussing the driver 10 in detail, a better view of the distal tip of the shaft 3 is shown in FIG. 2.

Figure 2:
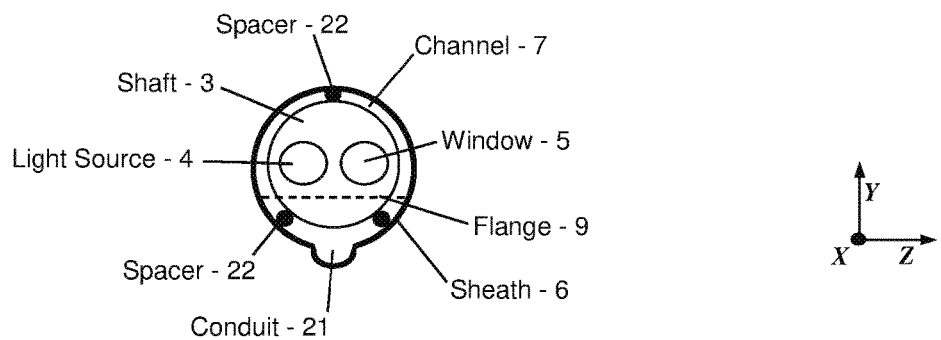
FIG. 2 is a schematic diagram depicting an end view of a distal tip of the endoscope of FIG. 1.
Figure 7:
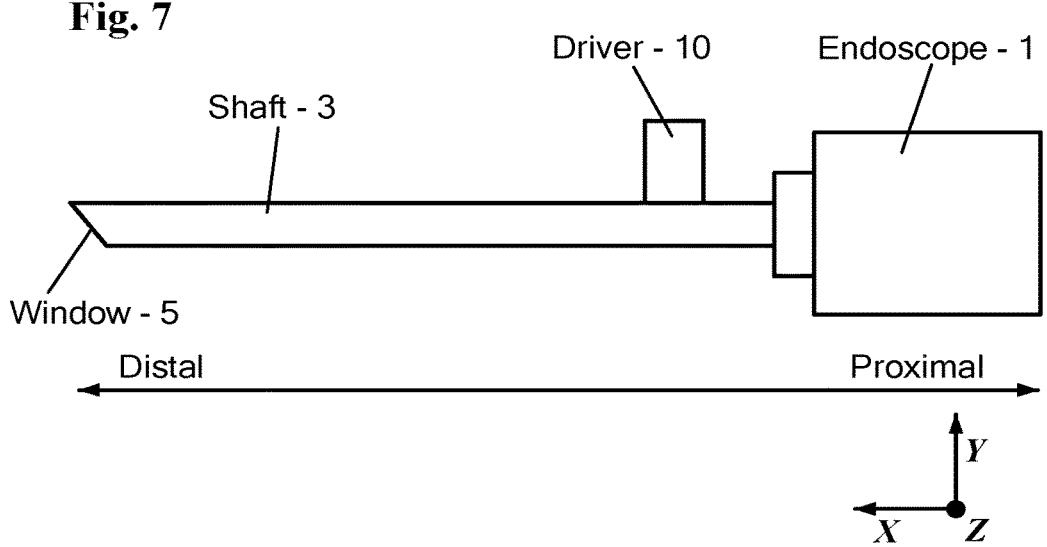
FIG. 7 is a schematic diagram depicting a side view of an exemplary endoscope without a sheath.

Referring to FIG. 2, the distal tip of the shaft 3 is shown. As may be seen in this example, the distal tip includes window 5. A light source 4 may accompany the window 5 and provide for illumination of the surgical site. The shaft 3 is generally surrounded by channel 7 established by an outer sheath 6. The channel 7 is reliably established by a plurality of spacers 22. Generally, the spacers 22 are provided in a geometry and patterning such that flow of irrigating fluid within the channel 7 is substantially unimpeded during operation. Accordingly, the spacers 22 may appear as dimples, bumps, striations or in other similar form. In this example, the distal tip of the sheath 6 is complemented with the flange 9. As shown also in FIG. 1, the flange 9 may be oriented such that irrigating fluid is directed toward the window 5 when commanded. Flow of irrigating fluid may be enhanced by incorporation of conduit 21 into sheath 6. Generally, the conduit 21 provides for increased volume of irrigating fluid that flows to the window 5 (when compared with a sheath 6 that is not equipped with the conduit 21).

Generally, the shaft 3 and the surrounding sheath 6 are designed to be flexible and of a limited diameter. That is, the shaft 3 and surrounding sheath 6 are designed to be unobtrusively ported to a surgical site. For example, the shaft 3 and sheath 6 may be easily inserted into a patient through an arthroscopic procedure for providing a practitioner with visual cues regarding the surgical site.

Figure 3:
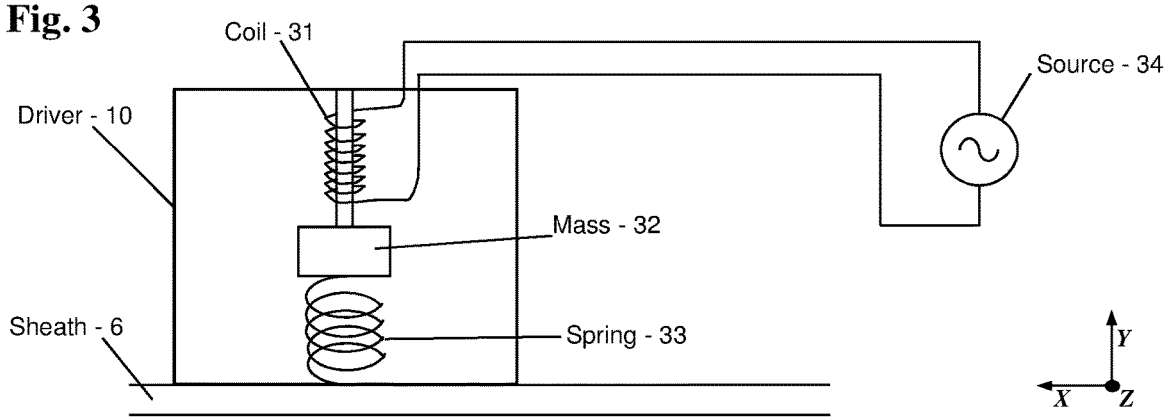
FIGS. 3-5 are cutaway schematic diagrams depicting embodiments of a driver for the endoscope of FIG. 1; and, FIG. 6 depicts transverse waves produced by the driver for the exemplary endoscope of FIG. 1.
Figure 4:
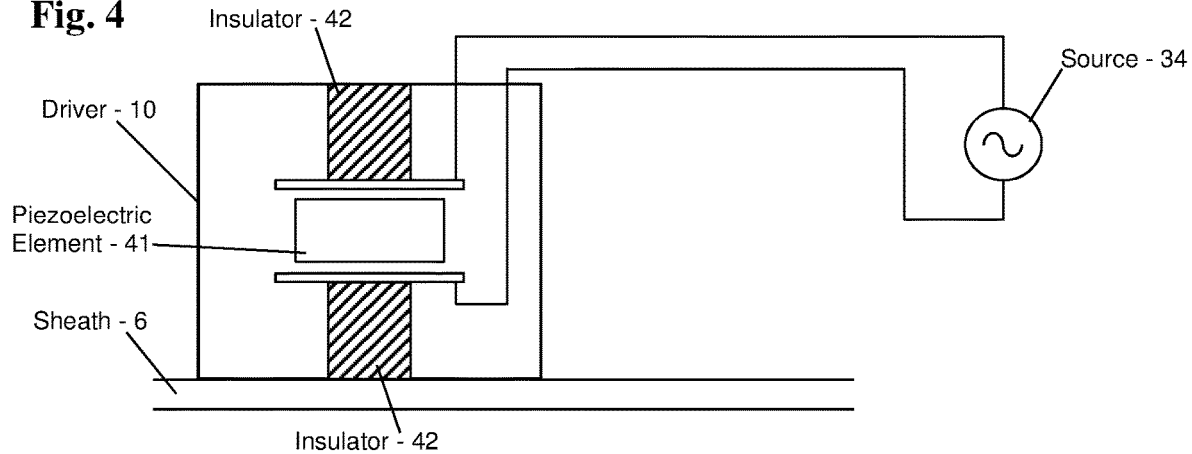
Figure 5:
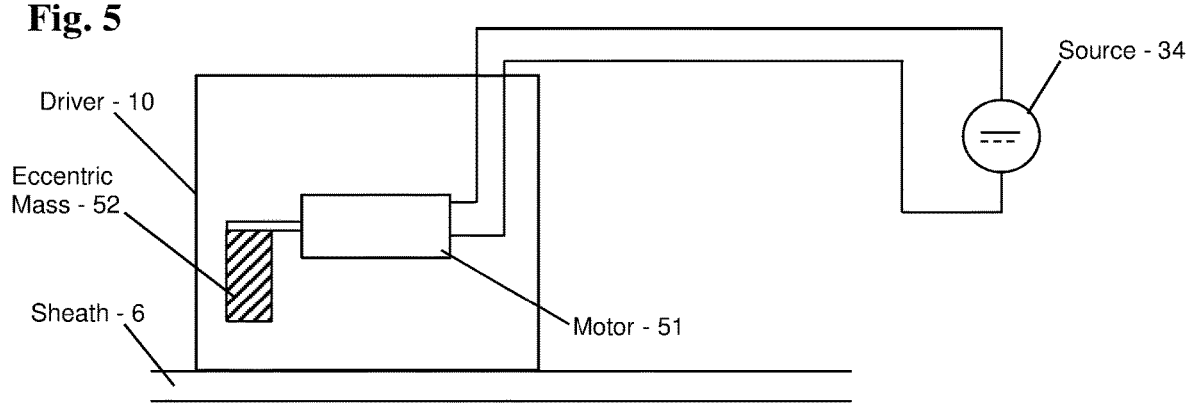

Referring now to FIGS. 3-5, there are shown exemplary and non-limiting embodiments of the driver 10. The driver 10 contains apparatus for generating transverse waves in the sheath 6. In general terms, the driver 10 is mounted at a proximal end of the sheath 6 and transmits vibrational energy to the sheath 6, and thus creates transverse waves within the sheath 6 (and therefore the shaft 3 secured within the sheath 6). The driver 10 is implanted upon or secured to the sheath 6, or generally mated with the sheath 6 in a manner that is adequate for communicating vibrational energy generated by the driver 10.

A first exemplary embodiment of the driver 10 is shown in FIG. 3. In this example, apparatus for generating transverse waves include a coil 31, a mass 32, and a spring 33. Generally, the coil 31 is driven by an external source 34. The source 34 may include, for example, a frequency generator (e.g., a source of alternating current (AC)). Output of the source 34 causes the coil 31 to repel the mass 32. The spring 33 receives energy delivered by the mass 32 and in turn repels the mass 32 back to the coil. By varying output of the source 34, a rate of oscillation of the mass 32 may be adjusted and controlled.

Another exemplary embodiment of the driver 10 is shown in FIG. 4. In this example, the driver 10 includes a piezoelectric element 41. The piezoelectric element 41 includes a piezoelectric crystal. The piezoelectric element 41 is mounted using insulators 42 as standoffs. The piezoelectric element 41 is driven by external source 34, which may provide, for example, alternating current (AC).

A further exemplary embodiment of the driver 10 is shown in FIG. 5. In this example, the driver 10 includes a motor 51 and an eccentric mass 52. The eccentric mass 52 is connected to a shaft of the motor 51. In this example, the source 34 may provide alternating current (AC) or direct current (DC) as appropriate.

Generally, in each embodiment of the driver 10, a series of pulses of suitable periodic frequency and amplitude are delivered to the sheath 6. The pulses delivered are controllable through, for example, user controls to vary output of the source 34.

Figure 6:
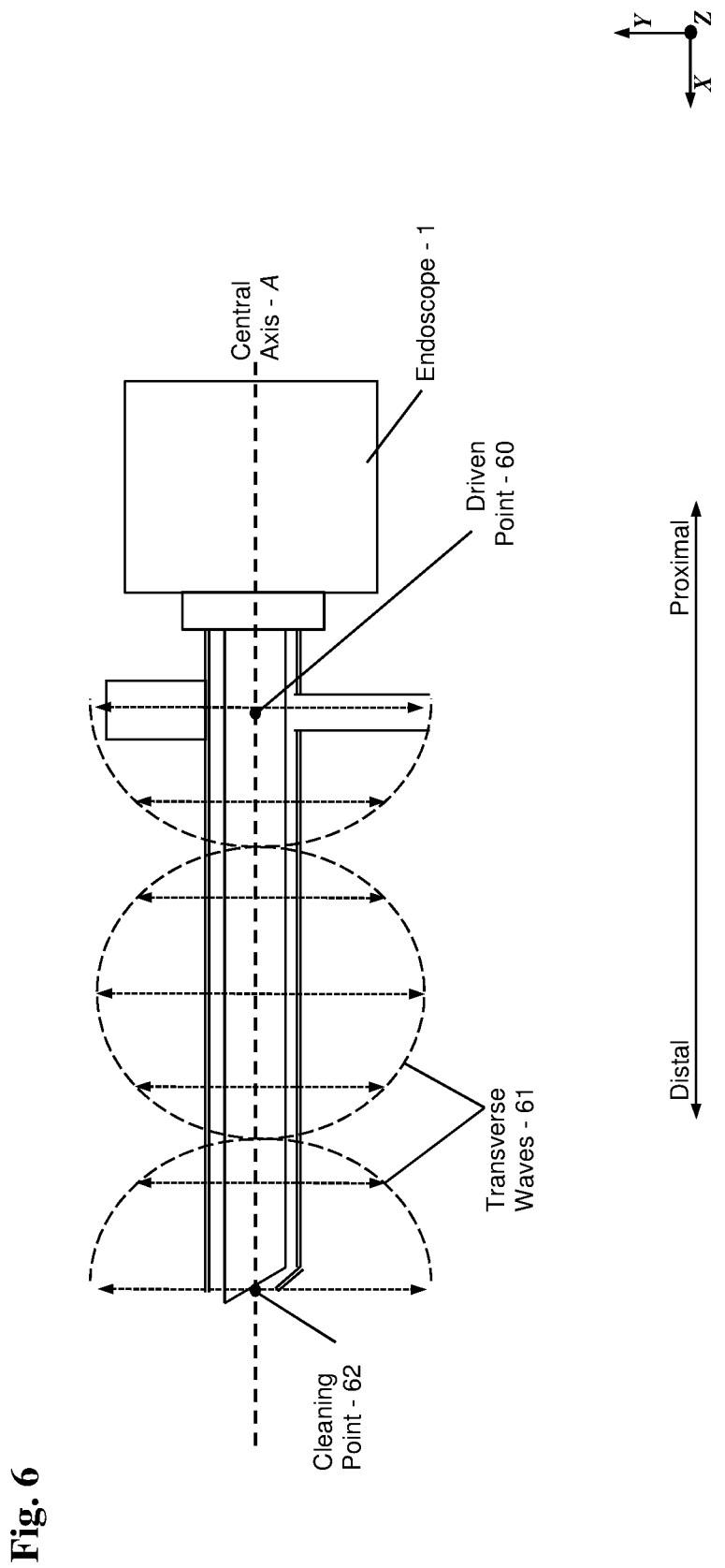

Refer now also to FIG. 6, where a relationship between transverse waves produced by the driver 10 and the shaft 3 of the endoscope 1 is shown.

In this illustration, the driver 10 drives the transverse waves about a driven point 60. The driven point 60 is centered along a central access, A. By tuning the driver 10 (such as by adjusting the source 34), the practitioner can drive a plurality of transverse waves 61 along a length of the shaft 3, such that the maximum amplitude is reached at a cleaning point 62 (i.e., the distal tip of endoscope 1). In general, the frequency and amplitude of the source 34 are controlled to produce a periodic driving force transverse to the axis of the shaft 3 of the endoscope 1. The driver 10 transmits mechanical energy to the sheath 6 at a proximal location along the sheath 6.

Generally, the driver 10 is located at an anti-node for standing transverse waves along the sheath 6 and the shaft 3. The frequency produced by the source 34 may be chosen to produce an integral number of half wave lengths, such that the distal tip of the sheath 6 and shaft 3 are located at or near an anti-node. In the example shown in FIG. 6, the wavelength equals the distance from the driver 10 to the distal tip of the endoscope 1. This forces the distal tip to undergo transverse oscillations. The motion of the distal tip provides the necessary inertial forces to disperse residual liquid from the window 5.

Generally, a cleaning cycle calls for injecting irrigating liquid into the port 8, which then flushes contamination from the window 5; and then turning on the source 34 for an interval that is adequate to disperse any material adhering to the window 5. The cleaning cycle may be terminated when the practitioner using the endoscope 1 is satisfied with the results (such as by visual inspection of the surgical site).

The frequency chosen to drive the driver 10 need only produce an integral number of standing waves along the sheath 6. The example shown includes one full wave, merely for purposes of clarity. Any number of full wavelength from one on up could be employed.

Having introduced aspects of the system for cleaning the distal tip of an endoscope during use, some additional aspects and embodiments are now introduced.

In general, the sheath 6 is manufactured for a specific model of endoscope 1. Accordingly, the sheath 6 is of a predetermined length, and of materials that exhibit known properties. Accordingly, the driver 10 may be configured (i.e., "tuned") to correctly work with the specific embodiment of the endoscope 1.

The sheath 6 may be manufactured to cooperate with the driver 10. For example, materials and construction of the sheath 6 may be selected for transmission of the transverse waves created by the driver. Additionally, the sheath 6 may include mounting features (a "mount," not shown) designed to accommodate mounting of the driver 10 to the sheath 6.

In some embodiments, the driver 10 is supplied as a separate system. That is, the driver 10 may be supplied (with the source 34 and other equipment as appropriate) such that the driver 10 is separate from the sheath 6. More specifically, and by way of example, the driver 10 may be supplied as a reusable component that may be attached to a disposable component (i.e., the sheath 6). Accordingly, the sheath 6 may be configured for receiving the driver 10. More specifically, and by way of example, the sheath 6 may include a connecting or securing feature that is built into each sheath 6.

In some embodiments, the source 34 includes components for providing a particular cleaning cycle. For example, the source 34 may include electronics for slewing frequency of the driver 10 from some initial frequency through to a second frequency. This may be performed for a predetermined number of cycles. In doing so, the anti-node would move along the length of the shaft 3. At some point, the anti-node would pass the distal tip and produce the necessary transverse motion to disperse material adhering to the window 5. This process may be configured for any combination of sheaths 6 and endoscopes 1.

Accordingly, the source 34 may include other components as appropriate for operating the driver 10. Components include user controls, a display, memory, a processor (or a microprocessor), at least one power supply, and machine executable instructions stored on machine readable media and configured to execute a method. Exemplary methods include steps for completion of particular cleaning cycles. By way of example, the source 34 may include an equipment selector which permits a practitioner to select a particular model of endoscope 1. By selecting the particular model of endoscope 1, the source 34 may adjust internal parameters such as frequency, amplitude and the like for performing a standardized cleaning cycle developed for that model of endoscope 1.

In some embodiments, the driver 10 (and ancillary equipment) is configured for a sheathless shaft 3. That is, the driver 10 may be configured for a "dry" implementation, or an implementation that does not make use of irrigating fluid dispensed through a channel 7.

In some embodiments, the driver 10 (and ancillary equipment) are included in the endoscope 1 as equipment coming from the original equipment manufacturer.

Accordingly, for the driver 10 (and ancillary equipment) may be provided as a retrofit to an existing endoscope 1, as a complement to an existing endoscope 1, or as a part of an endoscope 1.

As discussed herein, the driver 10, the source 34, and any ancillary equipment deemed appropriate by a user, manufacturer, designer or other similarly interested party provide for an "electronic endoscope cleaner." Accordingly, an electronic endoscope cleaner provides for fulfillment of the functions described herein in terms of the driver 10 and the source. Additionally, the electronic endoscope cleaner may be configured as described herein, or in a variety of other ways as may be devised by one skilled in the art.

As discussed herein, the term "clean" as well as the term "cleaning" generally refers to clearing the window 5 on the distal tip of the endoscope 1 from foreign material that distorts or degrades images obtained through the window 5. Adequate clearing of the window 5 is to be judged by a user, a practitioner, a manufacturer, designer or other similarly interested party.

Various other components may be included and called upon for providing for aspects of the teachings herein. For example, additional materials, combinations of materials and/or omission of materials may be used to provide for added embodiments that are within the scope of the teachings herein.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. Apparatus for cleaning a distal tip of an endoscope, the apparatus comprising:
    a shaft of the endoscope; and
    a driver configured to be mounted in contact with the shaft of the endoscope, where the driver is configured to generate transverse waves along a length of the shaft such that the transverse waves cause a physical transverse movement proximate the distal tip of the endoscope to effect a physical cleaning of the distal tip.

2. The apparatus as in claim 1, further comprising a sheath mounted over the shaft, wherein the driver is configured to be mounted onto the sheath.

3. The apparatus as in claim 2, wherein a fluid channel is disposed between the sheath and the shaft.

4. The apparatus as in claim 2, wherein the sheath comprises a port for receiving irrigating fluid.

5. The apparatus as in claim 1, wherein the driver comprises a spring, a coil, and a mass.

6. The apparatus as in claim 1, wherein the driver comprises a piezoelectric element.

7. The apparatus as in claim 1, wherein the driver comprises a motor coupled to an eccentric mass.

8. The apparatus as in claim 1, wherein a source for powering the driver is user controllable.

9. The apparatus as in claim 1, wherein the driver is adjustable for providing transverse waves of varied amplitude and frequency.

10. The apparatus as in claim 1, wherein the driver is configured for mounting proximal to the endoscope and producing a transverse wave comprising an anti-node at a distal tip of the endoscope.

* * * * *